(12) United States Patent
Hale et al.

(10) Patent No.: US 10,092,169 B2
(45) Date of Patent: *Oct. 9, 2018

(54) SOLID STATE VARIABLE DIRECTION OF VIEW ENDOSCOPE

(71) Applicant: Karl Storz Imaging, Inc., Goleta, CA (US)

(72) Inventors: Eric L. Hale, Vancouver, WA (US); Hans David Hoeg, Washington, DC (US); George E. Duckett, III, Castaic, CA (US); Nathan Jon Schara, Washougal, WA (US)

(73) Assignee: KARL STORZ IMAGING, INC., Goleta, CA (US)

( * ) Notice: Subject to any disclaimer, the term of this patent is extended or adjusted under 35 U.S.C. 154(b) by 362 days.

This patent is subject to a terminal disclaimer.

(21) Appl. No.: 14/538,308

(22) Filed: Nov. 11, 2014

(65) Prior Publication Data

US 2015/0065799 A1 Mar. 5, 2015

Related U.S. Application Data

(63) Continuation-in-part of application No. 14/312,146, filed on Jun. 23, 2014, now Pat. No. 8,992,423, which
(Continued)

(51) Int. Cl.
*A61B 1/00* (2006.01)
*A61B 1/04* (2006.01)
(Continued)

(52) U.S. Cl.
CPC ........ *A61B 1/00183* (2013.01); *A61B 1/0005* (2013.01); *A61B 1/00006* (2013.01);
(Continued)

(58) Field of Classification Search
CPC ............ A61B 1/00163; A61B 1/00174; A61B 1/00179; A61B 1/00181; A61B 1/00002;
(Continued)

(56) References Cited

U.S. PATENT DOCUMENTS

| 4,692,608 A | 9/1987 | Cooper et al. |
| 4,858,002 A | 8/1989 | Zobel |

(Continued)

FOREIGN PATENT DOCUMENTS

| EP | 0286733 A2 | 10/1988 |
| EP | 1774895 A1 | 4/2007 |

(Continued)

OTHER PUBLICATIONS

European Search Report Application No. EP 13 15 4405 Completed: Mar. 7, 2014; dated Mar. 18, 2014 8 pages.
(Continued)

*Primary Examiner* — Alexandra L Newton
*Assistant Examiner* — Pamela F Wu
(74) *Attorney, Agent, or Firm* — Michael Joseph Loi

(57) ABSTRACT

An endoscope with a wide angle lens that comprises an optical axis that is angularly offset from a longitudinal axis of the endoscope such that the optical axis resides at an angle greater than zero degrees to the longitudinal axis. The wide angle lens system simultaneously gathers an endoscopic image field, the endoscopic image field at least spanning the longitudinal axis and an angle greater than ninety degrees to the longitudinal axis. The endoscope includes an optical lens system to at least partially even out the information density across an imaging surface area of the imager.

26 Claims, 10 Drawing Sheets

Related U.S. Application Data is a continuation of application No. 13/721,297, filed on Dec. 20, 2012, now Pat. No. 8,758,234, which is a continuation-in-part of application No. 12/169,290, filed on Jul. 8, 2008, now Pat. No. 8,814,782.

(51) Int. Cl.
*G02B 23/24* (2006.01)
*H04N 5/225* (2006.01)

(52) U.S. Cl.
CPC ...... *A61B 1/00009* (2013.01); *A61B 1/00039* (2013.01); *A61B 1/00096* (2013.01); *A61B 1/00177* (2013.01); *A61B 1/00179* (2013.01); *A61B 1/00188* (2013.01); *A61B 1/042* (2013.01); *G02B 23/243* (2013.01); *G02B 23/2484* (2013.01); *H04N 2005/2255* (2013.01)

(58) Field of Classification Search
CPC . A61B 1/00096; A61B 1/00177; A61B 1/042; A61B 1/05; G02B 23/2407; G02B 23/2415; G02B 23/2423; G02B 23/243
USPC .......................................................... 600/176
See application file for complete search history.

(56) References Cited

U.S. PATENT DOCUMENTS

| | | | |
|---|---|---|---|
| 4,947,827 A | 8/1990 | Opie et al. | |
| 5,005,957 A | 4/1991 | Kanamori et al. | |
| 5,058,568 A | 10/1991 | Irion | |
| 5,185,667 A | 2/1993 | Zimmermann | |
| 5,313,306 A * | 5/1994 | Kuban .............. | G06F 17/30017 348/240.99 |
| 5,339,799 A | 8/1994 | Kami et al. | |
| 5,359,363 A | 10/1994 | Kuban et al. | |
| 5,384,588 A | 1/1995 | Martin et al. | |
| 5,604,530 A * | 2/1997 | Saito .................... | H04N 9/045 348/70 |
| 5,700,236 A | 12/1997 | Sauer et al. | |
| 5,800,341 A | 9/1998 | McKenna et al. | |
| 5,818,527 A | 10/1998 | Yamaguchi et al. | |
| 5,836,946 A | 11/1998 | Diaz et al. | |
| 5,902,232 A | 5/1999 | Igarashi | |
| 5,954,634 A | 9/1999 | Igarashi | |
| 6,002,430 A | 12/1999 | McCall et al. | |
| 6,224,542 B1 | 5/2001 | Chang et al. | |
| 6,294,775 B1 | 9/2001 | Seibel et al. | |
| 6,364,830 B1 | 4/2002 | Durell | |
| 6,371,909 B1 | 4/2002 | Hoeg et al. | |
| 6,449,103 B1 | 9/2002 | Charles | |
| 6,572,538 B2 | 6/2003 | Takase | |
| 6,648,817 B2 | 11/2003 | Schara et al. | |
| 6,663,559 B2 | 12/2003 | Hale et al. | |
| 7,221,522 B2 | 5/2007 | Tesar et al. | |
| 7,344,494 B2 | 3/2008 | Hoeg et al. | |
| 7,382,399 B1 | 6/2008 | McCall et al. | |
| 7,429,259 B2 | 9/2008 | Cadeddu et al. | |
| 2001/0019361 A1 | 9/2001 | Savoye | |
| 2002/0080248 A1 | 6/2002 | Adair et al. | |
| 2002/0136474 A1 | 9/2002 | Ammann et al. | |
| 2003/0114731 A1 | 6/2003 | Cadeddu et al. | |
| 2003/0163029 A1 | 8/2003 | Sonnenschein et al. | |
| 2004/0021929 A1 | 2/2004 | Nishioka | |
| 2004/0127769 A1 | 7/2004 | Hale et al. | |
| 2005/0058360 A1 | 3/2005 | Berkey et al. | |
| 2005/0113643 A1 | 5/2005 | Hale et al. | |
| 2005/0177026 A1 | 8/2005 | Hoeg et al. | |
| 2005/0197535 A1 * | 9/2005 | Hoeg ................. | A61B 1/00039 600/173 |
| 2006/0030751 A1 | 2/2006 | Uesugi et al. | |
| 2006/0069311 A1 | 3/2006 | Sullivan | |
| 2006/0203361 A1 * | 9/2006 | Kato ..................... | G02B 13/06 359/793 |
| 2006/0206006 A1 | 9/2006 | Schara et al. | |
| 2006/0252995 A1 | 11/2006 | Hoeg et al. | |
| 2006/0256431 A1 | 11/2006 | Hoeg et al. | |
| 2006/0256450 A1 | 11/2006 | Tesar et al. | |
| 2007/0043352 A1 | 2/2007 | Garrison et al. | |
| 2007/0047103 A1 | 3/2007 | Fujisaki | |
| 2007/0195425 A1 | 8/2007 | Arai | |
| 2007/0225690 A1 | 9/2007 | Sekiguchi et al. | |
| 2008/0021282 A1 | 1/2008 | Hoeg et al. | |
| 2008/0051655 A1 | 2/2008 | Sato et al. | |
| 2008/0091064 A1 | 4/2008 | Laser | |
| 2008/0091069 A1 | 4/2008 | Groszmann | |
| 2008/0161642 A1 | 7/2008 | Hale et al. | |
| 2008/0174820 A1 | 7/2008 | Furuhashi et al. | |
| 2008/0266441 A1 | 10/2008 | Ichimura | |
| 2008/0269779 A1 | 10/2008 | Cadeddu et al. | |
| 2009/0012407 A1 | 1/2009 | Zuluaga et al. | |
| 2009/0096865 A1 | 4/2009 | McKinley | |
| 2009/0253955 A1 | 10/2009 | Akiba | |
| 2010/0076268 A1 | 3/2010 | Takasugi et al. | |
| 2011/0046637 A1 | 2/2011 | Patel et al. | |
| 2011/0105844 A1 | 5/2011 | Sullivan et al. | |
| 2011/0301414 A1 | 12/2011 | Hotto et al. | |

FOREIGN PATENT DOCUMENTS

| | | |
|---|---|---|
| EP | 2143374 A1 | 1/2010 |
| JP | 2066511 A | 3/1990 |
| JP | H06308381 A | 11/1994 |
| JP | 10290777 A | 11/1998 |
| JP | 2000325307 A | 11/2000 |
| JP | 2005328970 A | 12/2005 |
| JP | 2007509710 A | 4/2007 |
| WO | 2005041755 A2 | 5/2005 |

OTHER PUBLICATIONS

European Search Report; EP 09 16 4962; dated Sep. 17, 2009; 6 pages.

* cited by examiner

*Prior Art*

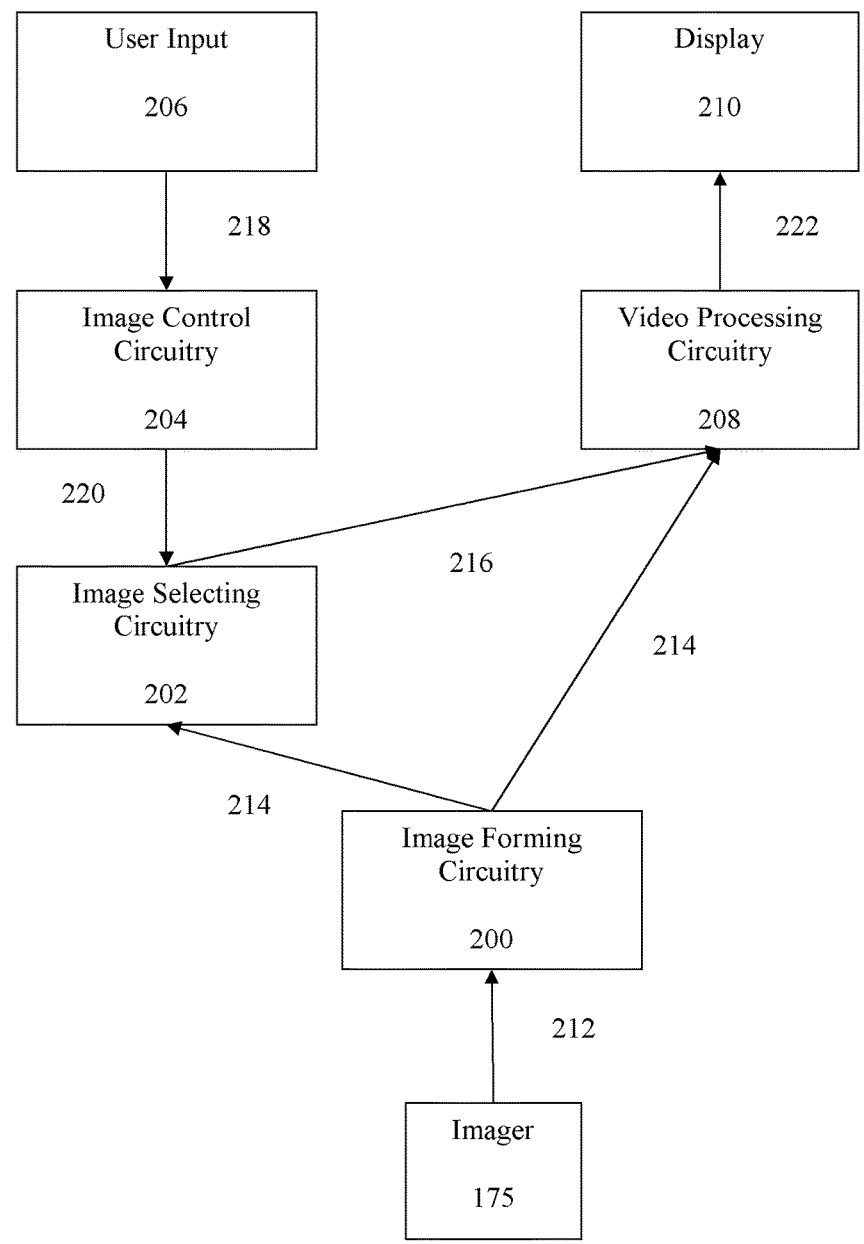

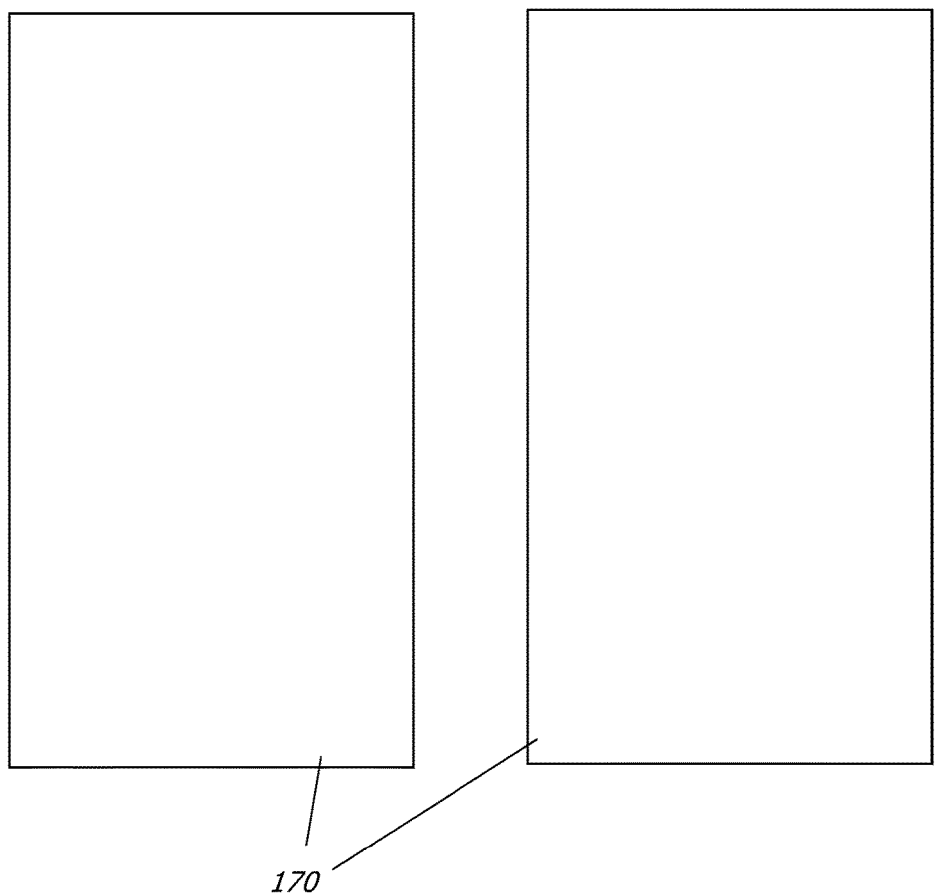

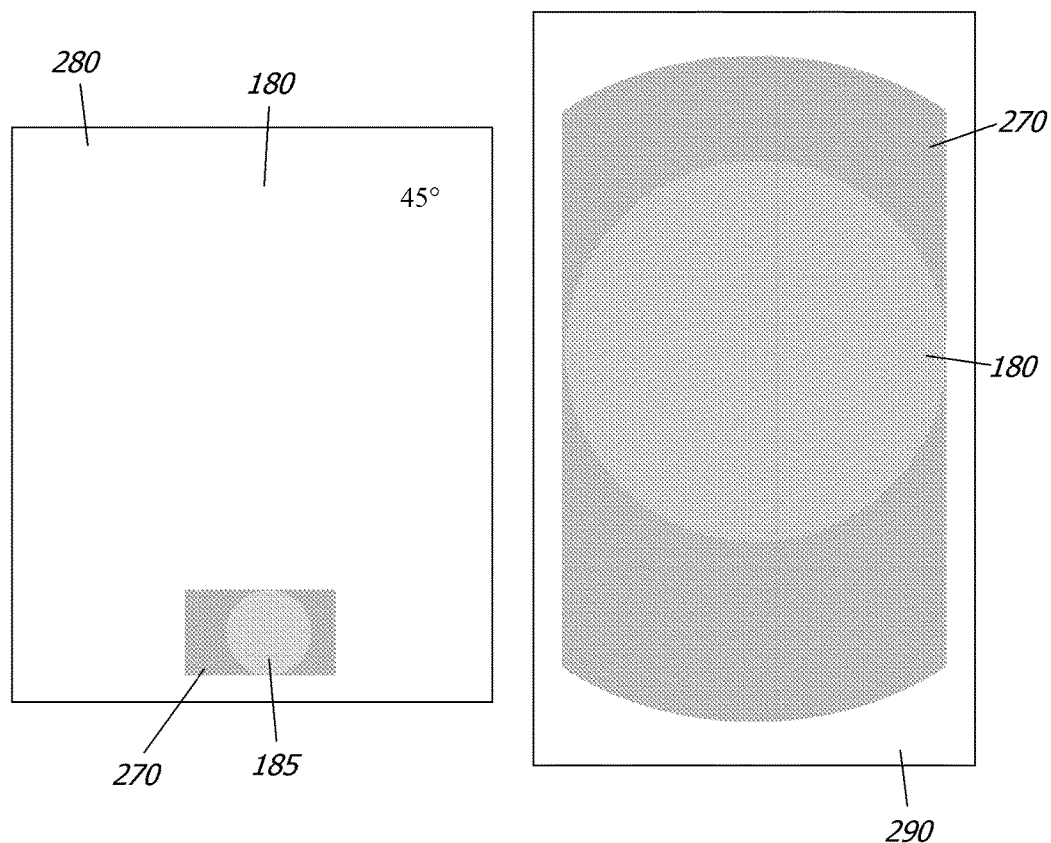

SOLID STATE VARIABLE DIRECTION OF VIEW ENDOSCOPE

FIELD OF THE INVENTION

The present invention relates to variable direction of view endoscopes, in particular, variable direction of view endoscopes incorporating solid state imagers and wide-angle lens systems. The present invention includes using a lens system to at least partially even out the information density across an imaging surface area.

BACKGROUND OF THE INVENTION

Variable direction of view endoscopes allow a user to change the endoscopic viewing direction without having to change the position of the endoscope itself. Such endoscopes are useful when a user wants to see structures which are beside or behind the tip of the endoscope but cannot easily move the endoscope shaft because of anatomical constraints or constraints imposed by other surgical instruments in the operative field.

Variable direction endoscopy is desirable because it affords surgeons greater flexibility in their procedural approach. Increased viewing mobility improves the quality of diagnoses, as in cystoscopy for example, where a typical diagnostic screening involves inspecting the interior surface of the bladder for lesions or tumors. The ability to look laterally and retrograde is important when doing this type of diagnosis because it makes it possible to visually cover the entire bladder surface, including the entrance region near the bladder neck. In ear-nose-throat and neurosurgical procedures, variable viewing is desired because the procedures are delicate, and the entrance ports are small. It is therefore not possible to manipulate the endoscope significantly without injuring the patient. The ability to look sideways and backwards is important however during and after tumor resection when it is necessary to keep track of tumor fragments, which if not caught can nucleate new tumors. Laparoscopy, another surgical discipline, imposes fewer maneuvering constraints but still benefits markedly from variable direction viewing because it allows surgeons to get better observation angles during a procedure and increases diagnostic capabilities. Also, because of the greater viewing versatility, variable direction of view endoscopes can minimize conflicts with other tools and can simplify surgical planning by their ability to achieve standard viewing angles from nonstandard positions, allowing the surgeon to keep the endoscope "off to the side" but still acquire the desired view.

A fundamental feature of variable direction endoscopy is that it generally makes it possible for surgeons to eliminate "blind movements." A blind movement is the process of moving an instrument inside a patient without being able to see where the instrument is heading. This can occur when it is necessary to advance a fixed-angle side viewing endoscope in its length direction without being able to see what is ahead of the scope, or when a surgical tool has to be manipulated at the boundary of the endoscopic field of view.

Many known variable direction of view endoscopes also have drawbacks. First, these scopes use a movable image sensor or optical element at the tip of the scope to vary the viewing direction. Because of these moving parts, fabricating variable direction of view scopes is complicated and costly, and such scopes are less robust than traditional fixed-angle scopes. Also, they often deliver inferior illumination and image quality.

These scopes, both rigid and flexible tip endoscopes, also subject the user to disorientation. As the endoscopic line of sight is changed, the user faces two difficulties. The first is keeping track of where the endoscope is "looking." With a rigid fixed-angle endoscope it is relatively easy for the user to extrapolate the endoscopic viewing direction from the position of the endoscope shaft. This is not the case when the viewing direction is regularly changed relative to the longitudinal axis of the endoscope; the user quickly loses track of spatial orientation within the anatomy being observed. The second difficulty is keeping track of what is "up" in the endoscopic image. Depending on the view-changing mechanism, the image will rotate relative to the surroundings, and the user frequently loses visual orientation. This disorientation is often not correctable, especially in variable direction of view scopes which have distal imagers and no facility for changing image orientation.

Given the difficulties of variable direction endoscopes, it is common for surgeons to utilize rigid endoscopes with fixed viewing angles. Surgeons rely heavily on knowing that a certain endoscope provides a 30 or 45 degree viewing angle. This preference for using multiple fixed angle endoscopes is due in part to the fact that a surgeon knows that for a particular endoscope they can dependably know what the anatomy should look like. FIGS. 1A, 1B, 1C and 1D show the distal ends of four commercially available endoscopes 10, 20, 30, 40 with the most commonly used viewing directions (view vectors) 50 corresponding to angular offsets from the longitudinal endoscope axis 60 of 0, 30, 45, and 70 degrees. Different surgical procedures typically require endoscopes of most of these angles with specific emphasis on one of them, often the 30 degree endoscope because it provides both a good forward view and a certain amount of lateral viewing. However, in most procedures, such as ear-nose-throat, bladder, orthopedic, brain, and abdominal procedures, lateral and partial retroviewing is beneficial and can be vital. Unfortunately surgeons often try to make due with only one or two scopes because changing the endoscope mid procedure is cumbersome (both light and camera cables have to be disconnected and reconnected), time consuming, and sometimes dangerous. Also, inserting off-angle endoscopes can be dangerous because they are not "looking" in the direction they are being inserted. This is a problem in neurosurgery, where surgeons often will not use 45- or 70-degree endoscopes because they are afraid of blindly thrusting the endoscope into delicate tissue.

Several designs have been proposed that provide solid state variable direction of view endoscopes to reduce or eliminate the number of moving parts. U.S. Pat. Nos. 5,185,667 and 5,313,306 disclose using a fish-eye lens that provide a hemispherical field of view, i.e. the lens provides a wide angle image that provides variable viewing in both the x and y directions. U.S. Pat. No. 6,449,103 discloses the use of an endoscope with a catadioptric system. U.S. Pat. No. 5,800,341 discloses an endoscope with charged coupled devices (CCDs) forming a circumferential band about the distal portion of the endoscope or CCDs covering substantially all of the outer side wall of the shaft adjacent to the distal end. U.S. Pat. No. 5,954,634 discloses the use of an image sensor at the proximal end of the endoscope that can move in a direction perpendicularly to the optical axis to enable selected portions of the image field to be viewed. However, these solutions can be considered deficient because they either provide poor resolution compared to a standard 70 degree field of view system, are overly complex and not feasible to manufacture, do not provide retrograde viewing, i.e. viewing at an angle greater than 90 degrees relative to the axis of the endoscope in the distal direction, or still incorporate overly complex mechanics of design.

What is desired, therefore, is a variable direction of view endoscope that can provide a feasible design and reduce the number of moving parts. It is further desired to provide an endoscope that can also provide forward and retrograde viewing.

It is still further desired to provide an endoscopic system that enables a surgeon to utilize reliable standard endoscopic viewing angles and at the same time provide an overall field of view that encompasses the viewing range.

It is still further desired to provide a solid-state variable direction of view endoscope that has a resolution that is as high as the resolution of non-solid state variable direction of view endoscopes.

It is still further desired to provide a lens system in the solid-state variable direction of view endoscope that evens out the information density across an imaging surface area.

SUMMARY OF THE INVENTION

Accordingly, it is an object of the present invention to provide an endoscope with an optical system that provides for f-sin(theta) distortion or f-theta distortion. In certain embodiments, the optical system includes a wide-angle lens system that comprises an optical axis that is angularly offset from a longitudinal axis of the endoscope such that the optical axis resides at an angle greater than zero degrees to the longitudinal axis. In certain embodiments, the wide angle lens system simultaneously gathers light rays from an endoscopic image field, the endoscopic image field at least spanning the longitudinal axis and an angle greater than ninety degrees to the longitudinal axis. In certain embodiments, the wide angle lens system includes a lens that provides for f-sin(theta) distortion or substantially f-sin(theta) distortion incorporated within the endoscope.

In certain embodiments, a lens system is used to at least partially even out the information density across an imaging surface area. In certain embodiments, a wide-angle lens is used to at least partially even out the information density across an imaging surface area. In certain embodiments, a lens system or a wide-angle lens is used to even out all of the information density across an imaging surface area.

In certain embodiments, a transmission system is not needed in order to even out the information density across the imaging surface area. In certain embodiments, additional subsystems are not needed in order to even out the information density across the imaging surface area, as the objective lens, which is a wide angle lens in certain embodiments, is used to even out all of the information density across an imaging surface area.

In certain embodiments, the endoscope further comprises an imager comprising an imaging surface area that receives at least a portion of an endoscopic image transmitted by the wide angle lens system and produces output signals corresponding to the endoscopic image field and image forming circuitry that receives the output signal and produces an image signal. It is preferable that the imaging surface area is rectangular with the longitudinal dimension of the imaging surface area corresponding to the longitudinal dimension of the endoscopic image field.

In certain embodiments, the imager only receives a portion of an endoscopic image transmitted by the wide angle lens system. In this embodiment, the resolution of the image provided by the imager is able to be increased so that it becomes as high as the resolution provided by a non-solid state variable direction of view endoscope.

In certain embodiments, the image transmission system distributes the angle of incidence of the light rays gathered from the endoscopic field of view onto the image surface area in order to even out the information density across the imaging surface area. In certain embodiments, the image transmission system distributes substantially all of the light rays gathered from the wide angle lens system in the longitudinal direction to correspond to the imaging surface area. In certain embodiments, the longitudinal direction of the imager spans the diameter of the captured endoscopic image field.

It is another object of the invention to provide an endoscopic system with image selecting circuitry that receives the image signal and produces a region of interest signal that corresponds to a region of interest field that is less than the endoscopic image field. The region of interest field can correspond to standard endoscopic viewing angles of zero, thirty, forty-five, and seventy degrees. In certain embodiments, the endoscopic system can comprise image control circuitry that receives a region of interest field selection from a user input and produces a field control signal identifying the region of interest field. The image selecting circuitry receives the field control signal and produces the region of interest signal in accordance with the field control signal. The image selecting circuitry can rotate the image formed by the region of interest signal about the axis of the viewing angle in order to alleviate disorientation by the user when switching between standard endoscopic viewing angles.

In certain embodiments, the user input can enable a user to select at least one preset standard endoscopic viewing angle and instructs the image control circuitry to generate a field control signal in accordance with that selection. In certain embodiments, the user input can further enable a user to select a progressive adjustment and produces an adjustment signal that incrementally alters the region of interest.

In certain embodiments, the endoscopic system can still further comprise video processing circuitry that generates video signals on the basis of the image signal and/or region of interest video signal and output all image video signal or region of interest video signal respectively to a display. In certain embodiments, the video processing circuitry can also provide a combined video signal comprising a first frame displaying the region of interest video signal and a second frame displaying the all image video signal.

It is yet another object of the present invention for the endoscope to comprise a transmission system that distributes the angle of incidence of the light rays gathered from the endoscopic field of view on to the image surface area in order to at least partially even out the information density across the surface area. This can be provided by a lens system that distributes substantially the entire endoscopic image field in the longitudinal direction to correspond to the imaging surface area. In certain embodiments, the distortion of this lens system is of the f-sin(theta) type. F-sin(theta) distortion means that the radial height of an image at the sensor is proportional to the sine of the corresponding object angle from which it originated.

A lens capable of f-sin(theta) distortion provides for a uniform f-number across the image plane. Therefore, image illumination and MTF (in the diffraction limit) will be uniform.

In certain embodiments, the imager receives only a portion of the light rays gathered from the endoscopic field of view. This allows images received by the solid state variable direction of view endoscopes to approach the resolution of a non-solid state variable direction of view endoscope.

These and other objects of the invention are achieved by providing an endoscope, comprising: a lens system that comprises an optical axis that is angularly offset from a longitudinal axis of the endoscope where the optical axis resides at an angle greater than zero degrees to the longitudinal axis; said lens system simultaneously gathering an image field spanning the longitudinal axis and an angle greater than ninety degrees to the longitudinal axis; an imager having an imaging surface area, said imager receiving at least a portion of the image field and producing an output signal related to the image field; imaging circuitry that receives the output signal and produces an image signal; wherein said lens system at least partially redistributes the image field to even out an information density across the imaging surface area.

In certain embodiments, said lens system includes a wide-angle lens, said wide angle lens at least partially redistributing the image field to even out an information density across the imaging surface area.

In certain embodiments, a lens system or a wide-angle lens is used to even out all of the information density across an imaging surface area.

In certain embodiments, a transmission system is not needed in order to even out the information density across the imaging surface area. In certain embodiments, additional subsystems are not needed in order to even out the information density across the imaging surface area, as the objective lens, which is a wide angle lens in certain embodiments, is used to even out all of the information density across an imaging surface area.

In certain embodiments, the endoscope further comprises image selecting circuitry that receives the image signal and produces a region of interest signal that corresponds to a region of interest field that is less than the image field.

In certain embodiments, the endoscope further comprises an interface that enables a user to input an adjustment to the region of interest and produces an adjustment signal that alters the region of interest.

In certain embodiments, said interface enables a user to rotate the image formed by the region of interest signal.

In certain embodiments, said image selecting circuitry rotates the image formed by the region of interest signal.

In certain embodiments, the rotation of the image is about the axis of the viewing angle.

In certain embodiments, the endoscope further comprises video processing circuitry that generates a combined video signal comprising a first frame displaying a region of interest video signal and a second frame displaying an all image video signal.

In certain embodiments, the at least one lens distributes the image field in the longitudinal direction to correspond to the imaging surface area.

In certain embodiments, a longitudinal direction of the imager spans a diameter of the image field.

In certain embodiments, the imaging surface area is rectangular and comprises a longitudinal dimension that is aligned with a longitudinal dimension of the image field.

In certain embodiments, the imaging surface area is square, circular or oval.

In certain embodiments, the imaging surface area has an HD aspect ratio of 16:9.

In certain embodiments, the endoscope further comprises an image transmission system.

In certain embodiments, said image transmission system at least partially redistributes the image field to even out an information density across the imaging surface area.

Other objects of the invention are achieved by providing an endoscope, comprising: an optical system, the optical system including a wide angle lens system, the wide angle lens system having an optical axis that is angularly offset from a longitudinal axis of the endoscope such that the optical axis resides at an angle greater than zero degrees to the longitudinal axis, wherein the wide angle lens system simultaneously gathers light rays from an endoscopic image field, the endoscopic image field at least spanning the longitudinal axis and an angle greater than ninety degrees to the longitudinal axis; an imager comprising an imaging surface area that receives only a portion of an endoscopic image transmitted by the wide angle lens system and produces output signals corresponding to the endoscopic image field; and image forming circuitry that receives the output signal and produces an image signal, wherein said optical system at least partially redistributes the image field to even out an information density across the imaging surface area.

In certain embodiments, the endoscope further comprises image control circuitry that receives a region of interest field selection from a user input and produces a field control signal identifying the region of interest field; wherein the image selecting circuitry receives the field control signal and produces the region of interest signal in accordance with the field control signal.

In certain embodiments, the user input enables a user to select at least one preset standard endoscopic viewing angle and instructs the image control circuitry to generate a field control signal in accordance with that selection.

In certain embodiments, the endoscope further comprises an image transmission system.

In certain embodiments, said image transmission system at least partially redistributes the image field to even out an information density across the imaging surface area.

Other objects of the invention are achieved by providing an endoscope comprising: a shaft comprising a proximal end and a distal end and a longitudinal axis spanning the proximal end and the distal ends, the distal end of the shaft being flexible; a handle coupled to the proximal end of the shaft; a wide-angle lens disposed in the distal end of the shaft, the wide angle lens gathering an endoscopic image field, said wide-angle lens comprises having an optical axis that is angularly offset from a longitudinal axis of the endoscope such that the optical axis resides at an angle greater than zero degrees to the longitudinal axis; and a solid state imager comprising an imaging surface area that receives at least a portion of endoscopic image transmitted by the wide angle lens system and produces output signals corresponding to the endoscopic image field, the solid state imager disposed in the distal end of the shaft, the wide-angle lens being disposed distally to the solid state imager.

In certain embodiments, the endoscope further comprises image forming circuitry that receives the output signal and produces an image signal; image selecting circuitry that receives the image signal and produces a region of interest signal that corresponds to a region of interest field that is less than the endoscopic image field; and image control circuitry that receives a region of interest field selection from a user input and produces a field control signal identifying the region of interest field; wherein the image selecting circuitry receives the field control signal and produces the region of interest signal in accordance with the field control signal, wherein the region of interest field corresponds to a standard endoscopic viewing angle.

In certain embodiments, the user input enables a user to select at least one preset standard endoscopic viewing angle and instructs the image control circuitry to generate a field control signal in accordance with that selection.

In certain embodiments, the user input enables a user to select a progressive adjustment and produces an adjustment signal that incrementally alters the region of interest.

In certain embodiments, the adjustment signal incrementally alters the viewing angle above or below the at least one preset standard endoscopic viewing angle.

In certain embodiments, the adjustment signal incrementally expands the region of interest by incorporating pixels that longitudinally reside above the original area of the region of interest and incorporating these pixels into the region of interest signal.

In certain embodiments, the endoscope further comprises an image transmission system, the image transmission system at least partially redistributing the image field to even out the information density across the imaging surface area.

In certain embodiments, the wide-angle lens simultaneously gathers an endoscopic image field at least spanning the longitudinal axis and an angle greater than ninety degrees to the longitudinal axis.

This application incorporates by reference in their entirety the subject matter of U.S. patent application Ser. No. 14/312,146 filed Jun. 23, 2014; U.S. patent application Ser. No. 13/721,297, issued as U.S. Pat. No. 8,758,234; U.S. patent application Ser. No. 13/354,801, issued as U.S. Pat. No. 8,771,177; and U.S. patent application Ser. No. 12/169,290, issued as U.S. Pat. No. 8,814,782.

Other objects of the invention and its particular features and advantages will become more apparent from consideration of the following drawings and accompanying description.

BRIEF DESCRIPTION OF THE DRAWINGS

FIG. 2C is a schematic of the circuitry for an embodiment of the endoscopic system of the present invention that provides for image processing;

FIG. 3A is a depiction of information distribution upon an image sensor from a wide angle lens without image correction;

FIG. 3B is a depiction of information distribution upon an image sensor from a wide angle lens with image correction;

FIG. 4A is a depiction of a display generated by an embodiment of the endoscopic system of the present invention;

FIG. 4B is a depiction of another display generated by an embodiment of the endoscopic system of the present invention;

DETAILED DESCRIPTION OF THE INVENTION

The following detailed description illustrates the invention by way of example, not by way of limitation of the principles of the invention. This description will enable one skilled in the art to make and use the invention, and describes several embodiments, adaptations, variations, alternatives and uses of the invention, including what is presently believed to be the best mode of carrying out the invention.

Figure 7:
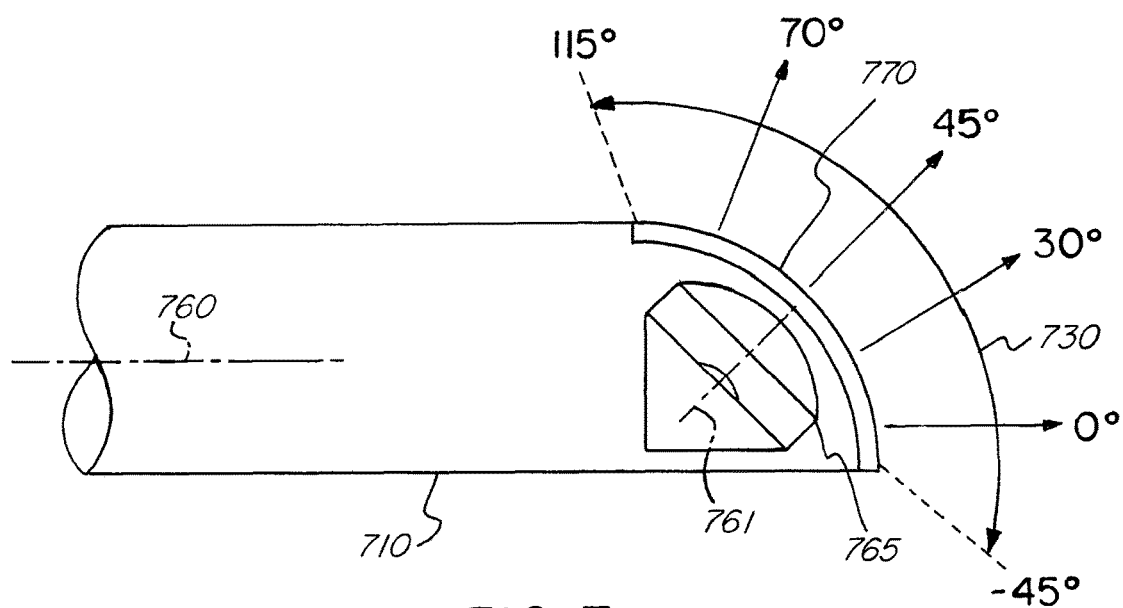
FIG. 7 is cross-section of the distal end of an embodiment of the endoscope of the present invention along the longitudinal axis.

FIG. 7 depicts a preferred embodiment of the present invention. FIG. 7 depicts a distal tip 710 of an endoscope with a longitudinal axis 760, a viewing window 770, and a wide angle lens system 765 with optical center. The optical center 761 is angularly offset from the longitudinal axis 760 of the endoscope 710 and covers a viewing range 130 of 160 degrees from −45 to +115 degrees relative to the longitudinal axis. From this configuration, the wide angle lens system 765 simultaneously gathers an endoscopic image field 730 that spans the longitudinal axis and an angle greater than ninety degrees to the longitudinal axis. As a result, the simultaneous image field gathered by the endoscope provides both forward and retrograde imaging. Providing a variable direction of view endoscope that spans this range is beneficial because it enables a user to view objects that reside in front of the endoscope and behind the standard fields of view for endoscopes. This improves the ability of a user to safely operate and handle the device in the body cavity. Further by incorporating a wide angle lens with an optical center that is angularly offset relative to the longitudinal axis, the endoscope will be able to more accurately mimic the viewing capabilities and function of a fixed angle endoscope.

Additionally, FIG. 7 shows an endoscope without utilizing a transmission system 150. Through testing, it was realized that an objective lens group, such as a wide angle lens, at least partially evens out the information density across an imaging surface area, and thus, in certain embodiments, a transmission system is not needed in order to even out the information density across the imaging surface area.

Figure 8:
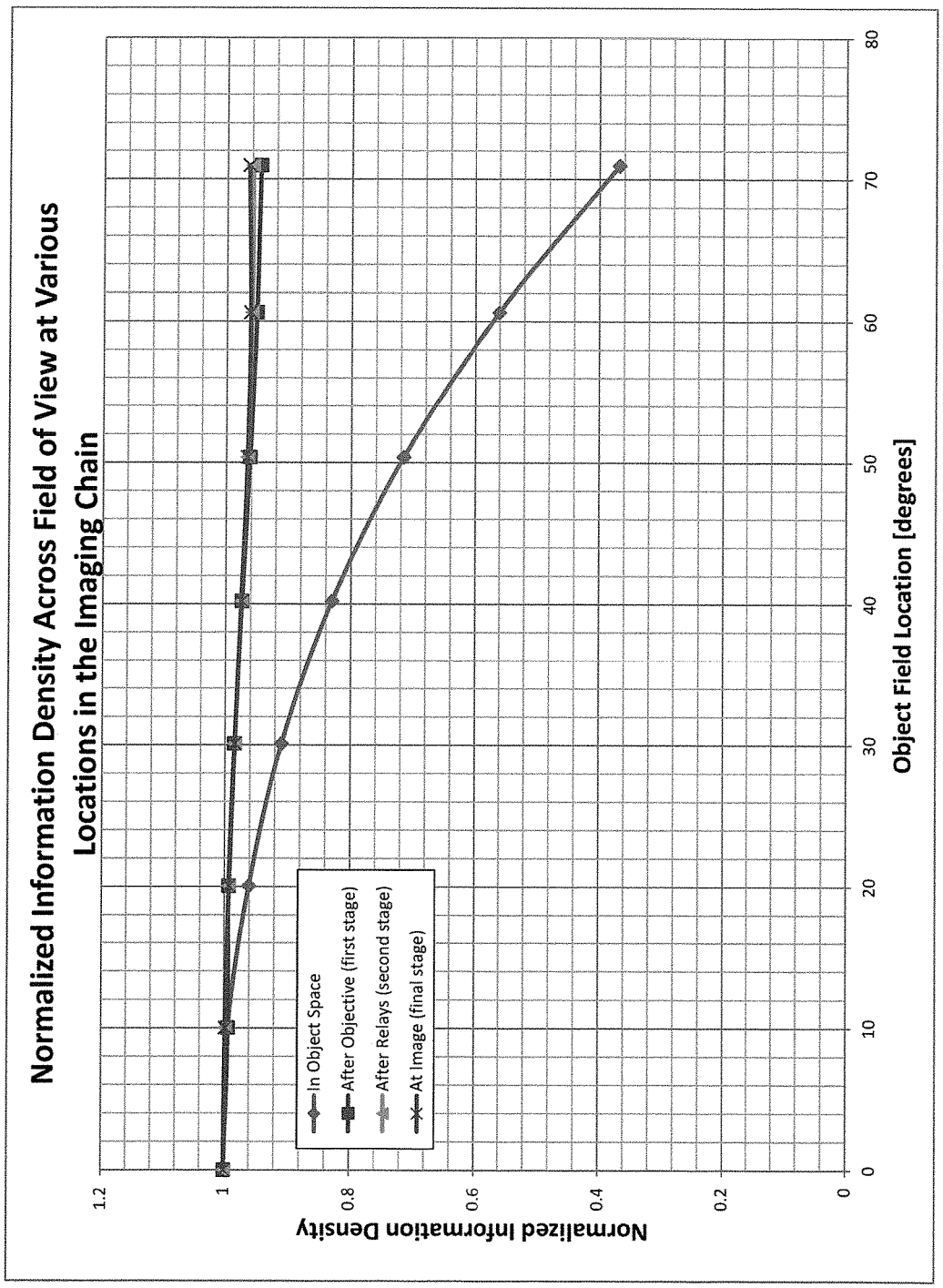
FIG. 8 is a graph of a normalized information density across the field of view at various locations in an image chain.

FIG. 8 shows a chart of the normalized information density across field of view at various locations in the image chain. As shown, the information density is not uniform in at the object itself, but is uniform after the objective lens or the wide angle lens. This demonstrates that the objective lens is doing substantial work in making the information density uniform.

In certain embodiments, the information density remains uniform going through the other subsystems. In other words, they generate no change in the information density, and all of the change in the information density occurs via the objective lens.

In other embodiments, the objective lens at least partially evens out the information density across an imaging surface area, and other subsystems are responsible for additional changes in the information density.

In certain embodiments, an image transmission system may be provided within the endoscope, such that the image transmission system at least partially evens out the information density across an imaging surface area and the objective lens also at least partially evens out the information density across an imaging surface area.

Figure 1A:
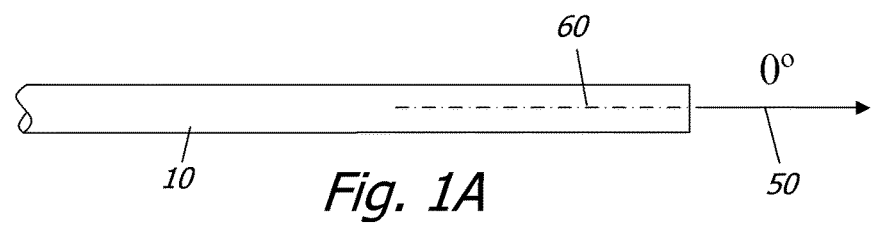
FIGS. 1A-D is a depiction of standard fixed angle endoscopic systems.
Figure 1B:
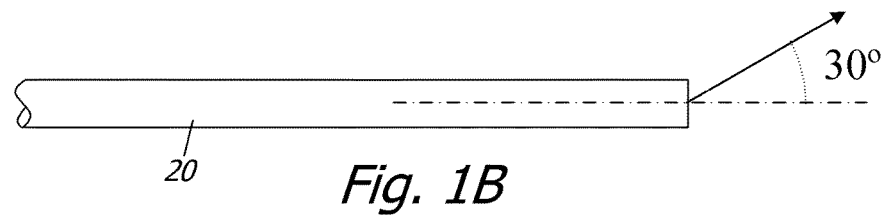
Figure 1C:
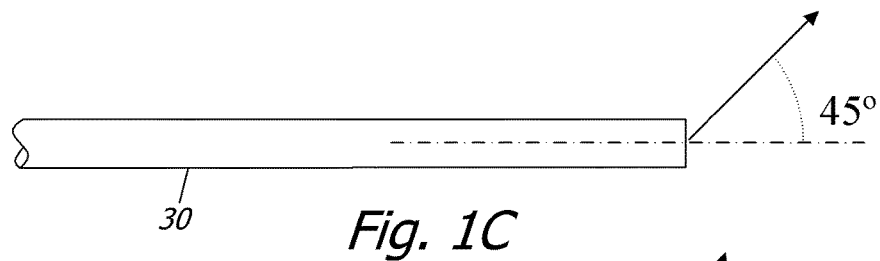
Figure 1D:
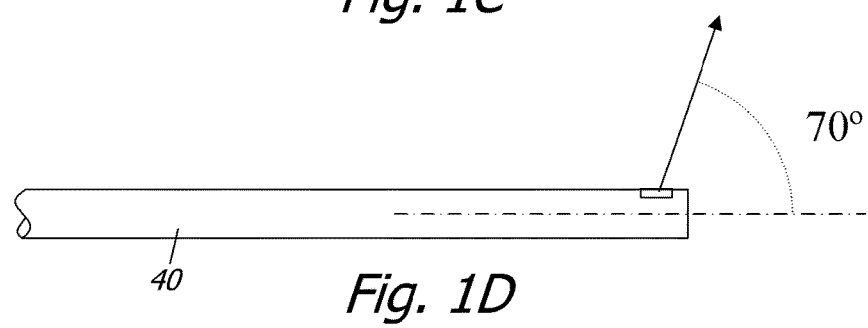
Figure 2A:
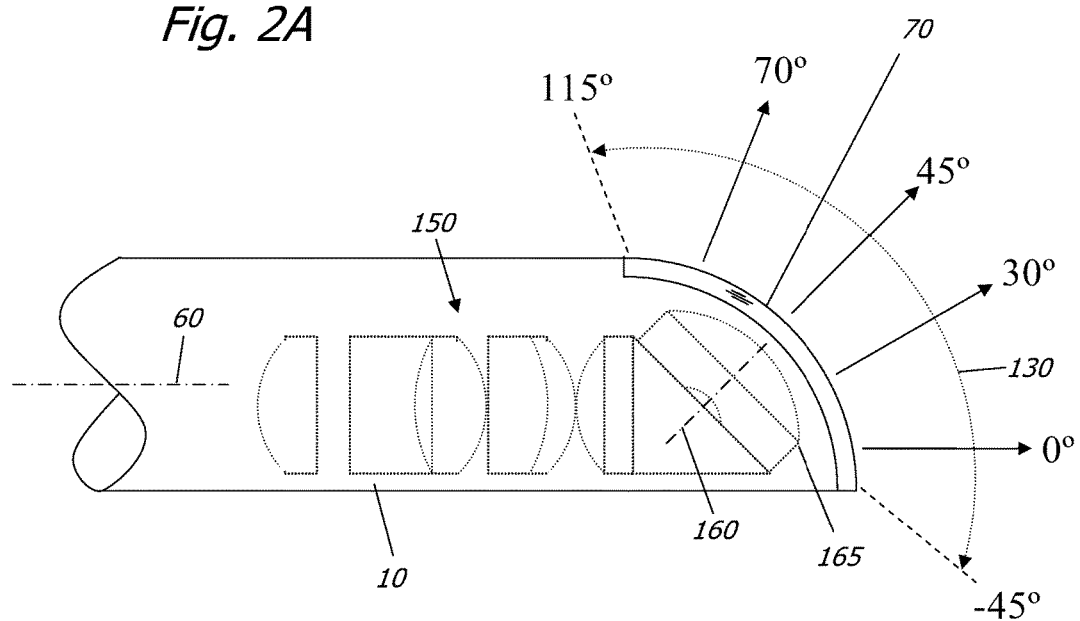
FIG. 2A is cross-section of the distal end of an embodiment of the endoscope of the present invention along the longitudinal axis.
Figure 2B:
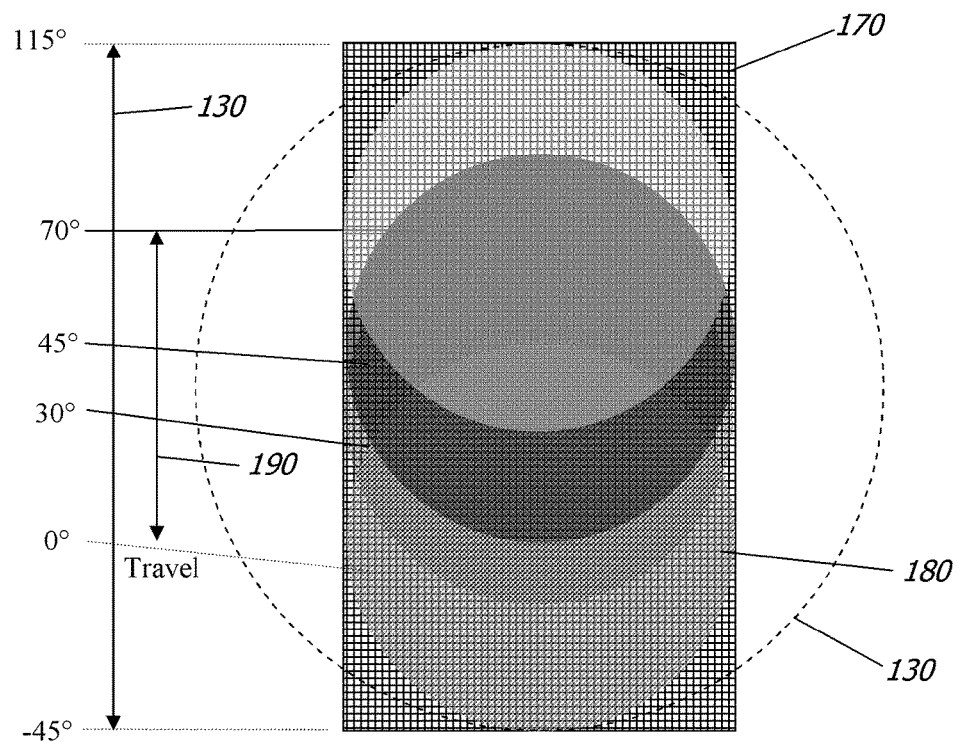
FIG. 2B is a depiction of the image sensor of an embodiment of the endoscope of the present invention relative to the endoscopic field of view.

FIGS. 2A and 2B depict a preferred embodiment of the present invention. FIG. 2A depicts a distal tip 10 of an endoscope with a longitudinal axis 60, a viewing window 70, a wide angle lens system 165 with optical center 160 and a transmission system 150. The optical center 160 is angularly offset from the longitudinal axis 60 of the endoscope 10 and covers a viewing range 130 of 160 degrees from −45 to +115 degrees relative to the longitudinal axis. From this configuration, the wide angle lens system 165 simultaneously gathers an endoscopic image field 130 that spans the longitudinal axis and an angle greater than ninety degrees to the longitudinal axis. As a result, the simultaneous image field gathered by the endoscope provides both forward and retrograde imaging. Providing a variable direction of view endoscope that spans this range is beneficial because it enables a user to view objects that reside in front of the endoscope and behind the standard fields of view for endoscopes. This improves the ability of a user to safely operate and handle the device in the body cavity. Further by incorporating a wide angle lens with an optical center that is angularly offset relative to the longitudinal axis, the endoscope will be able to more accurately mimic the viewing capabilities and function of a fixed angle endoscope. As discussed in more detail below, while wide angle lenses are beneficial in that they can increase the overall field of view, one deficiency is that they tend to provide an uneven information distribution over the overall field of view, i.e. the resolution of images obtained at angles further away from the optical axis will be diminished. As a result, a wide angle lens with an optical center that is angularly offset will enable the endoscope to produce higher resolution images at angles that correspond to standard fixed angle endoscopes. This will improve the willingness of surgeons to adopt and use variable direction of view endoscopes.

Furthermore, having a wide angle lens with an optical center that is angularly offset has been shown to at least partially even out the information density across an imaging surface area. Through unexpected testing, it was realized that an objective lens (such as a wide angle lens) provided the majority of the evening out of the information density across an imaging surface area.

The image field gathered by wide angle lens system 165 is conveyed to transmission system 150, which will be discussed in more detail below. Transmission system 150 in turn conveys the wide angle field of view to an image sensor that comprises image surface area 170. Image surface area 170 is formed by a plurality of pixels that gather and convert light into output signals. Image surface area 170 is preferably rectangularly shaped with a longitudinal dimension that is greater than its lateral dimension, but can also be a variety of different shapes, such as square, circular or oval. Also, it is preferable that the image surface area 170 has an HD aspect ratio of 16:9. Since a wide-angle lens system can provide uneven information distribution, without correction an HD image sensor enables the crowded information regions to be captured and displayed on a monitor. As shown in FIG. 2B, image surface area 170 partially captures field 130. It is preferable that the longitudinal dimension of image surface area 170 substantially correspond to the entire longitudinal dimension of field 130. This enables the endoscopic system to provide the user with an image or a range of regions of interest that span the field of view of the endoscope. However, image surface area 170 only captures a portion of the lateral dimension of field 130. The lateral dimension of area 170 can be chosen such that the distortion of an image laterally is minimal and not detected by the human eye. Further, by limiting the lateral dimension of the sensor, the cross-sectional area of the endoscope can be more efficiently used. For instance, the lateral dimension of the wide angle lens can be reduced and consequently reduce the overall size of the endoscope. Also, the area of the field of view not captured by the sensor can be used carry a fiber optic illumination system.

FIG. 2B also depicts specific regions of interest (ROIs) at 0, 30, 45 and 70 degrees which can be selected by a user over a range 190 and is discussed in more detail below. A region of interest is an image area formed on image surface area 170 that is a subset of the overall field of view captured by the sensor. The center of the area of the ROI corresponds to a selected longitudinal viewing angle chosen by a user. The overall area of the ROI can correspond to the field of view typically provided by a fixed angled endoscope for that same angle. Alternative, the overall area of the ROI can be chosen to provide a minimal distortion variation across the overall area. This can be achieved by providing image selecting circuitry that forms a region of interest signal based on a predetermined set of sensor pixels. Alternatively, this can be achieved by providing an image selecting circuitry that measures the degree of variance of an image signal for pixels that encompass the viewing angle and selects an area of the ROI based on a distortion tolerance. Still further, the overall area of the ROI can be chosen such that the field encompassed by a viewing angle at least partially overlaps with an adjacent standard viewing angle, such as 30 and 45 degrees. ROIs that are sized to overlap with adjacent viewing angles will assist a user in maintaining visual orientation in the event that a viewing angle is changed.

As shown in FIG. 2C, image sensor 175 produces output signals 212 that correspond to the endoscopic image field. Image forming circuitry 200 receives the output signals and converts the signals into image signals 214. Image signals 214 can be received by image selecting circuitry 202, which utilizes this signal to produce a region of interest signal 216. As discussed above, image selecting circuitry 202 forms ROI signal 216 by selecting the portions of the image signal 214 that correspond to the pixels of sensor 170 that surround a particular viewing angle within a given area. FIG. 2C also shows that the endoscopic system also comprises a user input 206, from which a user can select a region of interest viewing angle. When a user selects a region of interest viewing angle, input 206 transmits a region of interest field selection 218 that is received by image control circuitry 204. Image control circuitry 204 in turn produces a field control signal 220 identifying the ROI. The field control signal 220 is received by the image selecting circuitry 202, which generates a region of interest signal 216 in accordance with the field control signal 220.

Preferably input 206 enables a user to select preset standard endoscopic viewing angles and instructs the image control circuitry to generate a field control signal in accordance with that selection. It is preferable that the input 206 enables the user to select viewing angles corresponding to 0, 30, 45 and 70 degrees relative to the longitudinal axis of the endoscope.

It is also preferable that input 206 also provides a user with a nudge, or progressive adjustment, capabilities. In such an embodiment, input 206 can provide a selection 218 that incrementally alters the ROI such that the user can see a portion of a cavity just outside the field of view for the viewing angle. In one aspect, the input can provide a selection 218 that incrementally adjusts the viewing angle in the longitudinal direction above or below the current viewing angle, shifting the pixels selected to form the ROI signal. Alternatively, the input can provide a selection 218 that incrementally expands the area of the ROI in one longitudinal direction by incorporating additional pixels that reside in that direction in to the ROI signal. Another alternative is to for the input to provide a selection 218 incrementally expands the area of the ROI in both longitudinal directions by incorporating pixels that longitudinally reside outside the original area of the ROI and incorporating these pixels into the ROI signal. Giving a user the ability to nudge enables the user to look slightly beyond what is currently shown in the ROI. Today surgeons using a fixed angle endoscope sometimes operate on the edge of the view field with limited vision because the endoscope cannot be manipulated to achieve the necessary view. Slightly changing the orientation of a fixed angle endoscope or swapping one endoscope for another with a different viewing angle can be cumbersome and dangerous. By incorporating a nudge feature, the user is able to start from a standard endoscopic viewing angle and slightly shift the viewing angle to see what is outside the initial ROI. Also, if a preset view angle does not provide the necessary field of view, changing to another preset viewing angle will require the surgeon to visually reorient themselves. The nudge enables the surgeon to make a progressive change to the viewing angle and helps avoid visual disorientation.

Typically when a user switches between standard endoscopic viewing angles the user can become visually disoriented because the placement of common anatomy within a body cavity at the second viewing angle will differ from objects visualized at the first viewing angle. To address this problem, it is preferable that input 206 enables a user to rotate an image formed within a ROI. In such an embodiment, input 206 can provide a selection 218 to image control circuitry 204 to generate a field control signal 220 that instructs image selecting circuitry 202 to rotate the image produced by the region of interest signal 216 about the viewing angle axis. This embodiment enables a user to electronically correct the orientation of an endoscopic image in order to overcome any problems associated with visual disorientation.

The endoscopic system further includes video processing circuitry 208 that converts the region of interest signal 216 and/or image signal 214 into a video signal 222, which is received by a standard display 210. When the video processing circuitry 208 receives image signal 214, the processing circuitry generates an all image video signal. When the video processing circuitry 208 receives ROI signal 214, the processing circuitry generates a region of interest video signal.

FIG. 4A shows an embodiment of the image generated by video signal 222 on display 210. Display 210 provides a video image 280 that includes a first frame depicting the region of interest image 180 for a selected viewing angle, in this case 45 degrees, and a second frame that displays the all image video signal 270. It is preferable that the all image video signal 270 also include indicia 185 that show the location of the region of interest image 180 relative to overall field of view. Video image 280 is beneficial because in most surgical situations it is useful for the surgeon to have the largest view of the entire field possible. However, as discussed below, very large fields of view can be subject to significant distortion and are not always optimal to use for surgical visualization. When a large field 270 is coupled with a local view 180 associated with a ROI, it becomes useful because it helps the surgeon see where the selected ROI 180 is located in the global surgical landscape. FIG. 4B shows an alternative display scheme using a large monitor 290 which displays a global image 270 and simultaneously a full scale local image 180 on top of the global image.

In typical wide angle systems, the information density will vary across the captured field, i.e. for viewing angles that are further away from optical center 160, such as the 0 and 70 degree viewing angles depicted in FIG. 2A, the information density can be substantially less than optical center. When such a wide angle field of view is projected on to a solid state imager, such as a CCD or CMOS imager, the resolution of the field at these viewing angles can be noticeably poor. As shown in FIG. 3A, the information density across image surface area 170 is typically greater towards the center of the imager and can decrease substantially across the imager in the longitudinal directions. While the present invention can be implemented without adjusting for this difference in information density, it is preferable that endoscope 10 provide a transmission system 150 that distributes the image field to at least partially even out the information density across image surface area 170. To even out the information density and improve the resolution of the imager as shown in FIG. 3B, it is preferable that transmission system 150 is part of an f-theta optical system or an f-sin(theta) optical system.

An f-theta optical system uniformly separates the light rays incident to wide angle lens 165 by a distance proportional to f-theta, where f is the focal distance of the lens system and theta is the angle of incidence of the image rays relative to optical axis 160. The f-theta optical system provides a uniform distribution of the image field relative to the optical axis such that equivalent solid angles in the object will be imaged onto equivalently sized regions of the imaging area.

In an f-sin(theta) optical system the radial height of an image relative to the image location of the optical axis is proportional to the sine of the corresponding object angle from which it originated. An f-sin(theta) optical system provides a uniform f-number across the image plane, and therefore uniform illumination and potentially uniform MTF. An f-sin(theta) optical system is an aspect of the optical system as a whole and is not separable from the wide angle aspect. In wide angle lens systems, the plano-concave front element of the objective contributes most (but not all) f-sin(theta) and wide angle aspects. An f-sin(theta) optical system provides a larger field of view for the image that is displayed.

Figure 5:
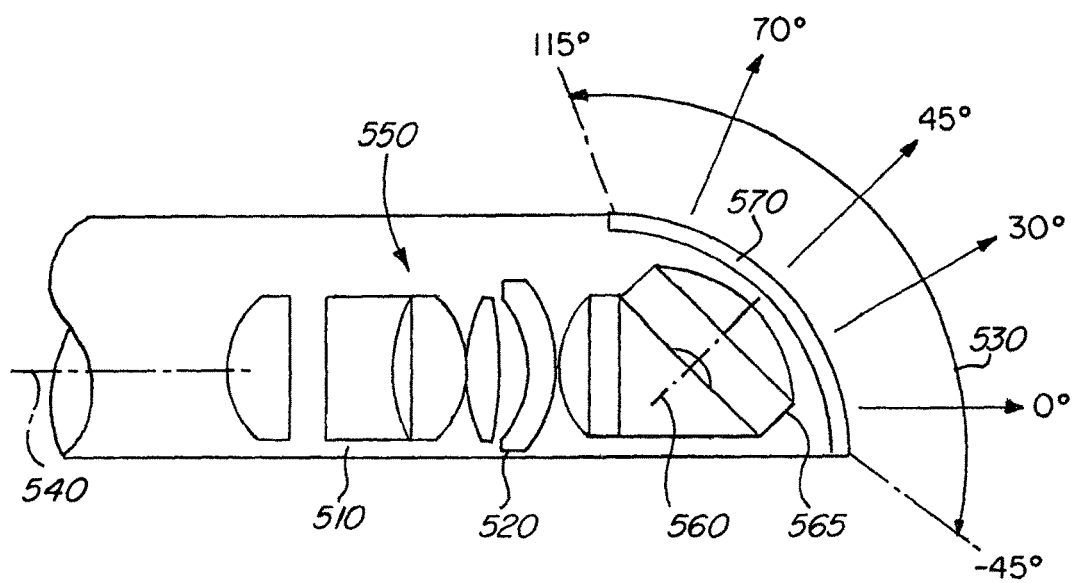
FIG. 5 is a cross-section of the distal end of the endoscope of the present invention along the longitudinal axis using a lens capable of f-sin(theta) distortion.

FIG. 5 depicts another preferred embodiment of the present invention. FIG. 5 depicts a distal tip 510 of an endoscope with a longitudinal axis 540, a viewing window 570, a wide angle lens system 565 with optical center 560 and a transmission system 550. The optical center 560 is angularly offset from the longitudinal axis 540 of the endoscope 510 and covers a viewing range 130 of 160 degrees from −45 to +115 degrees relative to the longitudinal axis. From this configuration, the wide angle lens system 565 simultaneously gathers an endoscopic image field 530 that spans the longitudinal axis and an angle greater than ninety degrees to the longitudinal axis. As a result, the simultaneous image field gathered by the endoscope provides both forward and retrograde imaging. Providing a variable direction of view endoscope that spans this range is beneficial because it enables a user to view objects that reside in front of the endoscope and behind the standard fields of view for endoscopes. This improves the ability of a user to safely operate and handle the device in the body cavity. Further by incorporating a wide angle lens with an optical center that is angularly offset relative to the longitudinal axis, the endoscope will be able to more accurately mimic the viewing capabilities and function of a fixed angle endoscope.

The image field gathered by wide angle lens system 565 is conveyed to transmission system 550, which will be discussed in more detail below. Transmission system 550 in turn conveys the wide angle field of view to an image sensor.

Transmission system 550 includes a doublet lens 520 or an achromatic doublet (double lens) 520. The doublet lens 550 is part of the lens system that is capable of providing f-sin(theta) distortion.

Figure 6:
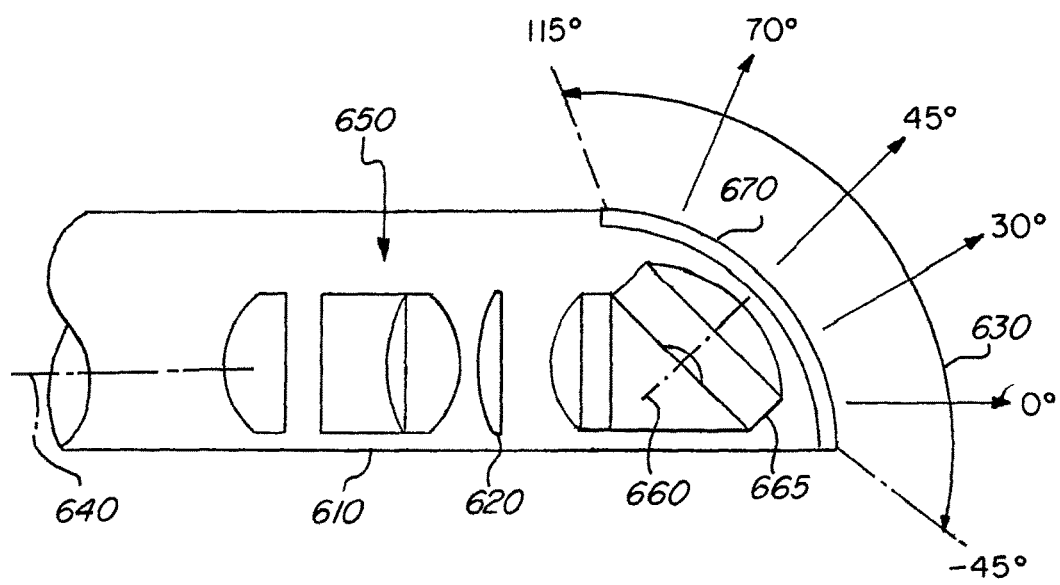
FIG. 6 is a cross-section of the distal end of the endoscope of the present invention along the longitudinal axis using a lens capable of f-sin(theta) distortion.

FIG. 6 depicts another preferred embodiment of the present invention. FIG. 6 depicts a distal tip 610 of an endoscope with a longitudinal axis 640, a viewing window 670, wide angle lens system 665 with optical center 660 and a transmission system 650. The optical center 660 is angularly offset from the longitudinal axis 640 of the endoscope 610 and covers a viewing range 130 of 160 degrees from −45 to +115 degrees relative to the longitudinal axis. From this configuration, the wide angle lens system 665 simultaneously gathers an endoscopic image field 630 that spans the longitudinal axis and an angle greater than ninety degrees to the longitudinal axis. As a result, the simultaneous image field gathered by the endoscope provides both forward and retrograde imaging. Providing a variable direction of view endoscope that spans this range is beneficial because it enables a user to view objects that reside in front of the endoscope and behind the standard fields of view for endoscopes. This improves the ability of a user to safely operate and handle the device in the body cavity. Further by incorporating a wide angle lens with an optical center that is angularly offset relative to the longitudinal axis, the endoscope will be able to more accurately mimic the viewing capabilities and function of a fixed angle endoscope.

The image field gathered by wide angle lens system 665 is conveyed to transmission system 650, which will be discussed in more detail below. Transmission system 650 in turn conveys the wide angle field of view to an image sensor.

Transmission system 650 includes a doublet lens 620 or an achromatic doublet (double lens) 620. The doublet lens 620 is part of the lens system that is capable of providing f-sin(theta) distortion.

If the optical system does not correct the variation in information density attributable to the wide angle lens system, then it may be necessary to provide circuitry that can correct any distortion or uneven information density that can be present in the image signal or the region of interest signal. However, by utilizing an f-theta optical system, the need to incorporate corrective circuitry and the complexities associated with such manipulation can be avoided.

The present invention merges the versatility of mechanical variable direction of view systems with the relative simplicity of solid state designs. The advantage of the present invention is that it provides a variable direction of view system that reduces or eliminates the need to use complex mechanical systems. The present invention also overcomes a number of disadvantages provided by typical wide angle endoscopic systems that incorporate solid state imagers. The present invention can provide a single instrument with no moving parts which provides the surgeon with all the standard and familiar viewing directions and ergonomics while maintaining excellent imaging performance.

The present invention has been described above in terms of a presently preferred embodiment so that an understanding of the present invention can be conveyed. However, there are alternative arrangements for a solid state variable direction of view endoscope. The scope of the present invention should therefore not be limited by the embodiments discussed, but rather it should be understood that the present invention is widely applicable to variable viewing direction instruments in general. All modifications, variations, or equivalent elements and implementations that are within the scope of the claims should therefore be considered within the scope of this invention.

What is claimed is:

1. An endoscope, comprising: a lens system that comprises an optical axis that is angularly offset from a longitudinal axis of the endoscope where the optical axis resides at an angle greater than zero degrees to the longitudinal axis; said lens system simultaneously gathering an image field spanning the longitudinal axis and an angle greater than ninety degrees to the longitudinal axis; an imager having an imaging surface area, said imager receiving at least a portion of the image field and producing an output signal related to the image field; imaging circuitry that receives the output signal and produces an image signal; image selecting circuitry that receives the image signal and produces a region of interest signal that corresponds to a region of interest field that is less than the image field; and an interface that enables a user to input an adjustment to the region of interest and produces an adjustment signal that expands the region of interest by incorporating pixels that reside outside an original area of the region of interest into the region of interest signal; wherein said lens system at least partially redistributes the image field to even out an information density across the imaging surface area.

2. The endoscope of claim 1, wherein said lens system includes a wide-angle lens, said wide-angle lens at least partially redistributing the image field to even out the information density across the imaging surface area.

3. The endoscope of claim 1, where said interface enables the user to rotate the image formed by the region of interest signal.

4. The endoscope of claim 1, where said image selecting circuitry rotates the image formed by the region of interest signal.

5. The endoscope of claim 4, where the rotation of the image is about the optical axis.

6. The endoscope of claim 1, further comprising video processing circuitry that generates a combined video signal comprising a first frame displaying a region of interest video signal and a second frame displaying an all image video signal.

7. The endoscope of claim 1, where a longitudinal direction of the imager spans a diameter of the image field.

8. The endoscope of claim 1, where the imaging surface area is rectangular and comprises a longitudinal dimension that is aligned with a longitudinal dimension of the image field.

9. The endoscope of claim 1, where the imaging surface area is square, circular, or oval.

10. The endoscope of claim 1, wherein the imaging surface area has an HD aspect ratio of 16:9.

11. The endoscope of claim 1, further comprising an image transmission system.

12. The endoscope of claim 11, wherein said image transmission system at least partially redistributes the image field to even out the information density across the imaging surface area.

13. An endoscope, comprising:
an optical system, the optical system including a wide-angle lens system, the wide-angle lens system having an optical axis that is angularly offset from a longitudinal axis of the endoscope such that the optical axis resides at an angle greater than zero degrees to the longitudinal axis, wherein the wide-angle lens system simultaneously gathers light rays from an endoscopic image field, the endoscopic image field at least spanning the longitudinal axis and an angle greater than ninety degrees to the longitudinal axis;

an imager comprising an imaging surface area that receives only a portion of an endoscopic image transmitted by the wide-angle lens system and produces output signals corresponding to the endoscopic image field;

image forming circuitry that receives the output signal and produces an image signal;

image selecting circuitry that receives the image signal and produces a region of interest signal that corresponds to a region of interest field that is less than the image field; and an interface that enables a user to input an adjustment to the region of interest and produces an adjustment signal that expands the region of interest by incorporating pixels that reside outside an original area of the region of interest into the region of interest signal;

wherein said optical system at least partially redistributes the image field to even out an information density across the imaging surface area.

14. The endoscope of claim 13, further comprising image control circuitry that receives a region of interest field selection from the interface and produces a field control signal identifying the region of interest field;

wherein the image selecting circuitry receives the field control signal and produces the region of interest signal in accordance with the field control signal.

15. The endoscope of claim 14, wherein the interface enables the user to select at least one preset standard endoscopic viewing angle and instructs the image control circuitry to generate a field control signal in accordance with that selection.

16. The endoscope of claim 13, further comprising an image transmission system.

17. The endoscope of claim 16, wherein said image transmission system at least partially redistributes the image field to even out the information density across the imaging surface area.

18. An endoscope, comprising:
a shaft comprising a proximal end and a distal end and a longitudinal axis spanning the proximal end and the distal ends, the distal end of the shaft being flexible;
a handle coupled to the proximal end of the shaft;
a wide-angle lens disposed in the distal end of the shaft, the wide-angle lens gathering an endoscopic image field, said wide-angle lens comprises having an optical axis that is angularly offset from a longitudinal axis of the endoscope such that the optical axis resides at an angle greater than zero degrees to the longitudinal axis;
a solid state imager comprising an imaging surface area that receives at least a portion of an endoscopic image transmitted by the wide-angle lens and produces output signals corresponding to the endoscopic image field, the solid state imager disposed in the distal end of the shaft, the wide-angle lens being disposed distally to the solid state imager;

image selecting circuitry that receives the image signal and produces a region of interest signal that corresponds to a region of interest field that is less than the image field; and an interface that enables a user to input an adjustment to the region of interest and produces an adjustment signal that expands the region of interest by incorporating pixels that reside outside an original area of the region of interest into the region of interest signal;

wherein the wide-angle lens simultaneously gathers the endoscopic image field at least spanning the longitudinal axis and an angle greater than ninety degrees to the longitudinal axis.

19. The endoscope of claim 18, further comprising: image forming circuitry that receives the output signal and produces an image signal; image control circuitry that receives a region of interest field selection from the interface and produces a field control signal identifying the region of interest field; wherein the image selecting circuitry receives the field control signal and produces the region of interest signal in accordance with the field control signal; wherein the region of interest field corresponds to a standard endoscopic viewing angle.

20. The endoscope of claim 19, wherein the interface enables the user to select at least one preset standard endoscopic viewing angle and instructs the image control circuitry to generate the field control signal in accordance with that selection.

21. The endoscope of claim 19, wherein the interface enables the user to select a progressive adjustment and produces an adjustment signal that incrementally alters the region of interest.

22. The endoscope of claim 21, wherein the adjustment signal incrementally alters the viewing angle above or below the at least one preset standard endoscopic viewing angle.

23. The endoscope of claim 21, wherein the adjustment signal incrementally expands the region of interest by incorporating pixels that longitudinally reside above the original area of the region of interest and incorporating these pixels into the region of interest signal.

24. The endoscope of claim 18, further comprising an image transmission system, the image transmission system at least partially redistributing the image field to even out the information density across the imaging surface area.

25. The endoscope of claim 1, wherein the adjustment signal incrementally expands the region of interest by incorporating pixels that reside outside the original area of the region of interest into the region of interest signal.

26. The endoscope of claim 1, wherein the adjustment signal expands the region of interest by incorporating pixels that longitudinally reside above the original area of the region of interest into the region of interest signal.

* * * * *